United States Patent [19]
Buheitel

[11] Patent Number: 6,116,250
[45] Date of Patent: Sep. 12, 2000

[54] PROCESS OF PERMANENT HAIR SHAPING

[75] Inventor: Horst Buheitel, Rehau, Germany

[73] Assignee: Wella Aktiengesellschaft, Darmstadt, Germany

[21] Appl. No.: 08/802,810

[22] PCT Filed: Jul. 20, 1996

[86] PCT No.: PCT/EP96/03216

§ 371 Date: Feb. 18, 1997

§ 102(e) Date: Feb. 18, 1997

[87] PCT Pub. No.: WO97/04738

PCT Pub. Date: Feb. 13, 1997

[51] Int. Cl.[7] .................................................. A45D 7/06
[52] U.S. Cl. ............................................ 132/205; 132/206
[58] Field of Search ..................................... 132/203, 204, 132/205, 206, 207

[56] References Cited

U.S. PATENT DOCUMENTS

| | | | |
|---|---|---|---|
| 2,624,347 | 1/1953 | Melaro | 132/205 |
| 4,214,596 | 7/1980 | Kaplan et al. | 132/204 |
| 4,660,580 | 4/1987 | Hoch et al. | 132/204 |
| 4,914,273 | 4/1990 | Matsui | 132/204 |
| 5,080,116 | 1/1992 | Ballard | 132/205 |
| 5,080,890 | 1/1992 | Ueno | 132/206 |
| 5,424,062 | 6/1995 | Schwan et al. | 132/204 |
| 5,437,860 | 8/1995 | Jarvis et al. | 132/205 |
| 5,570,708 | 11/1996 | Samain | 132/205 |

FOREIGN PATENT DOCUMENTS

| | | |
|---|---|---|
| 948186 | 9/1956 | Germany . |
| 972424 | 7/1959 | Germany . |
| 4117708A1 | 12/1991 | Germany . |

*Primary Examiner*—Todd E. Manahan
*Attorney, Agent, or Firm*—Michael J. Striker

[57] ABSTRACT

In the process for permanent shaping of hair, the hair is first rolled onto rollers and a permanent shaping composition based on a keratin reducing substance is applied to the rolled hair. The permanent shaping composition is allowed to act on the hair for 5 to 30 minutes and then rinsed out of the hair with water. The rollers are unrolled and removed from the hair and the hair is styled. During the styling the hair is combed into a desired shape with a comb, a brush or with the fingers, and at the same time or thereafter the tight hair end curl is transformed into a big curl wave with a comb, a brush or with the fingers and then the created hair style is dried at an elevated temperature. Alternatively the hair is combed into the desired hair style at elevated temperature by means of an appropriate device for hair styling at high temperature, particular a round brush heated electrically or by warm air or a round brush and a blow dryer. The styled hair is treated with a neutralizer based on an oxidizing agent and the neutralizer is rinsed out of the hair with water or washed out with a shampoo after it acts on the hair.

35 Claims, No Drawings

PROCESS OF PERMANENT HAIR SHAPING

The customary method for performing permanent hair shaping is based on two treatment steps: In the first step the cystine-disulfide-bridges of the hair keratin are unlocked by working in a preparation which contains and active reducing substance (shaping composition). Then the hair is shaped as desired. In a second step, cystine-disulfide-compounds are closed again by the use of a neutralizer, i.e. of a preparation containing oxidizing active substances.

From published European patent application 0 671 158 a process for permanent shaping of keratin materials is known, in which a permanent shaping composition on the basis of a hair keratin reducing substance is applied to the rolled hair, the treated keratin material is possibly given a heat treatment, the keratin material treated this way is rinsed out, the rinsed keratin material is left to rest and finally the rollers are removed. A neutralizer is not employed.

The wave resulting from this process is not satisfying because the hair still contains remainders of the reduction solution—which can lead to hair damage—and the resulting curl due to the missing oxidative re-bonding process is not sufficiently durable. A teaching in how a durable wave with big curls over the hair length can be evenly maintained is also not provided in this publication.

As the pioneering work in the German patent applications 948 186 and 972 424 shows, thioglycolic acid is used for example, as ammonium or monoethanol amino salt, as classical permanent reduction solution. Other common active reducing substances are inorganic sulfides, 2-mercapto propionic acid (thiolactic acid); 3-mercapto propionic acid, certain mercapto carboxylic acid esters, cysteine and derivatives of these compounds.

Both treatment steps as commonly practiced, i.e. the unlocking and the reconstruction of the cystine disulfide compounds, take place while the hair is on rollers. After the second step, the neutralizing step, the hair at first will show a tight curl in accordance with the size of the rollers. As a rule, such a tight curl is not desired, so that the result of the shaping process immediately has to be corrected again. Although the curl is satisfactory at the hairline in accordance with the process of the prior art, a friz results in the area of the middle shaft and at the hair ends. Therefore, a so-called "finger-wave treatment" employing hair rolling techniques and setting lotion resins for the creation of large, natural curls is necessary after each normal perm and each time the permed hair becomes moist. A lasting curl, in accordance with naturally wavy Central-European hair, cannot be achieved by means of the currently known perm processes. It is, however, the actual goal of the female and male clients requesting a perm treatment.

It is therefore the object to make a process of permanent hair shaping available, in which the disadvantages will be avoided and where moisture-resistant, simple, lasting, reliable and even permanent re-shaping of the hair into a final hairstyle without too tight a curl can be achieved. At the same time it should be possible, to be able to create or correct the desired size of the curl without pressure of time.

Therefore, the subject of the present invention as presented, is a process of permanent hair shaping, characterized in that:

a) the hair is rolled onto rollers,
b) a permanent shaping composition based on a hair keratin reducing substance is applied to the rolled hair,
c) the permanent shaping composition is left to act on the hair for 5 to 30 minutes,
d) the permanent shaping composition is rinsed out with water,
e) the rollers are unrolled and removed from the hair,
f) the hair is styled,
g) the styled hair is treated with a neutralizer based upon an oxidizing agent,
h) the neutralizer is rinsed out of the hair after its reaction time.

Preferably, the hair is washed with a commonly used shampoo prior to rolling it onto the rollers. Rinsing in accordance with treatment step h) preferably takes place with water, if necessary with the use of a shampoo.

In a particularly preferred embodiment of the process in accordance with the invention, the washed hair which has been preferably towel-dried, is treated with a balancing pre-wrap solution prior to rolling it onto the rollers. The balancing pre-wrap solution either is made from an active substance or contains an active substance which can be stored particularly in the damaged parts of the hair and thus reduces the action of the permanent shaping composition. This active substance is preferably a physiologically tolerated synthetic or natural hydrophobic oil or wax. Examples of such oils or waxes are jojoba oil, avocado oil, sunflower oil, wheat germ oil, montan wax, mineral wax, vaseline and paraffin.

The balancing pre-wrap solution consists preferably of a mixture of a physiologically tolerated synthetic or natural hydrophobic oil or wax and a solubilizer at a ratio of 50:1 to 2:1, preferably 40:1 to 10:1, or it contains at least 5 weight percent of this mixture. The solvent is preferably a compound ethoxilated with a 2 to 200, preferably 5 to 60 ethylene oxide group from the group of fatty acids, fatty acid ester, fatty acid amides, fatty acid amines or fatty alcohols with 6 to 30 carbon atoms. Suitable solvents are castor oils ethoxylated with 5 to 60 ethylene oxide groups, for example hydrated castor oils ethoxylated with 7 ethylene oxide groups (i.e. Arlacel$^{(R)}$ 989 of ICI), and hydrated castor oil ethoxylated with 40 ethylene oxide groups (i.e. Cremophor $^{(R)}$ RH40 of BASF).

It is of particular advantage, if the balancing pre-wrap solution consists of a mixture of physiologically tolerated synthetic or natural hydrophobic oil and hydrated castor oil ethoxylated with 40 ethylene oxide groups (i.e. Cremophor $^{(R)}$ RH40 of BASF) at a ratio of 50:1 to 2:1 or it contains at least 5 weight-% of this mixture.

It is particularly advantageous, if the balancing pre-wrap solution is allowed to react on the hair at a higher temperature, in particular at 30 to 45° C. For purposes of expediency an infrared device is used for this. The reaction time should be approximately 3 to 10 minutes. Afterwards the hair is rinsed with water.

The rollers used in the process of permanent hair shaping in accordance with the invention have a diameter of 5 to 20 mm depending on the desired wave and the texture of the hair. For thin, limp hair a roller thickness of 5 to 8 mm is particularly suitable, for medium-type hair a roller thickness of 8 to 10 mm and for thick hair a roller thickness of 10 to 20 mm would be suitable. If in doubt the choice of the roller should always be one size smaller. At completion of rolling, the permanent shaping composition is evenly applied to all rollers. It is advantageous to allow the permanent shaping composition to react at a higher temperature, particularly at 30 to 45° C. An infrared radiation device (i.e. in accordance with German Patent 40 18 186) or a dryer hood can be used for this. If a dryer hood is used, it is best to cover the hair with an aluminum foil cap beforehand to prevent escape of moisture or alkalizers, for example ammonia. At higher temperatures the reaction time with oxidatively untreated hair is 20 to 25 minutes and with oxidatively treated hair 15 to 20 minutes. It is most expedient to determine the reaction time of the permanent shaping composition by the use of a test roller in a manner known per se.

The hair keratin reducing substances contained in the permanent shaping composition are preferably employed as ready-to-use preparations for permanent hair shaping in an amount of 2 to 20 weight-%, particularly preferred in an amount of 2 to 12 weight-% and most preferred for use in an amount of 4 to 10 weight-%. Thioglycolic acid, thiolactic acid, cysteine, cysteamine, alkyl- or acyl-cysteamine or the salts of these compounds, for example, also thioglycolic acid ester or sulfides, particularly in an acid pH-range and also as a mixture together, can be used as hair keratin reducing substances.

The ready-to-use permanent shaping compositions have a preferred pH-value of 4 to 11, particularly preferred is a value from 7 to 9.5. As alkalizing agent or agent for setting the pH-value, ammonia or a sodium hydroxide solution are particularly considered, but also all other water-soluble, physiologically tolerated salts of organic and inorganic bases, as for example ammonium hydrogen carbonate.

The shaping reaction of the permanent shaping composition is chosen in such a way, that it is lower than is commonly necessary for the existing hair quality. For example, for regular fine hair with a pH=8.5 a thioglycolic acid concentration of 8 weight-% is commonly necessary. In accordance with the process of the invention, however, a permanent shaping composition is chosen, which only has approximately $\frac{2}{3}$ of the thioglycolic acid concentration commonly used, i.e. in this case only 6 weight-%. Thus it corresponds to a permanent shaping composition, which is commonly used for severely damaged hair through chemicals, i.e. oxidatively treated hair.

The permanent shaping composition can be produced as a one-, two-or three-component preparation, wherein the preparation can be present in form of an aqueous solution or an emulsion, as well as in a thickened water-based form, particularly as cream, gel or paste.

Thus the permanent shaping composition is for example available through the mixing of two components of which the first component contains at least an alkalizing agent, i.e. alkali carbonate, ammonium carbonate, alkali hydrogen carbonate or ammonium hydrogen carbonate, and the hair keratin reducing substance and the second component contains at least one of the cosmetic additives and water.

In addition it is possible, to package the permanent shaping composition in form a three-component preparation, wherein one component contains some of the cosmetic additives as well as water, a second, non-aqueous component contains the hair keratin reducing substance and the third component additional additives, such as perfume oil, solubilizers and care substances, in an aqueous solution or in non-aqueous form.

With all embodiments of the permanent shaping composition, the cosmetic additives can be contained in (an) aqueous as well as non-aqueous component(s). Of course the permanent shaping composition can contain all additives commonly used and known for such preparations, for example thickeners, such as bentonite, fatty acids, starch, polyacrylic acid and their derivatives, cellulose derivatives, alginates, vaseline, paraffin oils, wetting agents or emulsifiers of the category of anionic, cationic, amphoteric or non-ionogenic surfactants, for example fatty alcohol sulfates, fatty alcohol ether sulfates, alkyl sulfonates, alkyl benzene sulfates, quaternary ammonium salts, alkyl betaines, ethoxylated alkyl phenols, fatty acid alkanolamides or ethoxylated fatty acid esters; in addition opacifiers, for example polyethylene glycol ester; alcohols, for example ethyl alcohol, propyl alcohol, isopropyl alcohol and glycerin; sugar, for example D-glucose; solubilizers, stabilizers, buffer substances, perfume oils, pigments as well as hair conditioning and hair care components, as for example cationic polymers, lanolin derivatives, cholesterol, pantothenic acid and betaine.

The components referred to are used in the appropriate quantity commonly employed for these purposes, for example the wetting agents and emulsifiers in concentration of 0.2 to 30 weight-% in total, the alcohols in a quantity of 0.1 to 20 weight-% in total, the opacifiers, perfume oils and pigments in a quantity of 0.01 to 1 weight-% each, the buffer substance in a quantity of 0.1 to 10 weight-% in total, sugar, solubilizers, stabilizers, as well as hair conditioning and hair care components in a quantity of 0.1 to 5 weight-% each, while the thickeners and solubilizers can exist in this preparation at a quantity of 0.5 to 20 weight percent in total.

Also for increased effect, so-called swelling and penetration substances, as for example dipropylene glycol monomethyl ether, 2-pyrrolidone or 2-imidazolidinone, in a quantity of 1 to 30 weight-%, as well as for the prevention of excessive frizzing of the hair dithio compounds, for example dithiodiglycolic acid, dithio lactic acid, the dithioles of the compounds referred to or the respective salts, also in a quantity of 1 to 30 weight-%, can be added to this preparation.

As soon as the permanent shaping is sufficient, the permanent shaping composition is rinsed out with water. Preferably the rinsing process lasts 2 to 4 minutes. Thereafter it is advantageous to dab the rollers with an absorbent napkin or a towel.

Next the hair is unwound and the rollers are removed.

In a preferred embodiment of the process in accordance with the invention, a hair setting lotion on the basis of a hair setting polymer is now applied to the hair. The hair setting lotion can be a hair spray with or without propellant or it can be a so-called mousse. Hair sprays or mousses are generally available in form of an aqueous, water-alcohol based or alcohol-based mixture and contain 0.5 to 20 weight-% of a hair setting polymer. The hair setting lotion is preferably sprayed on.

These hair setting polymers are particularly the synthetic polymers polyvinyl pyrrolidone, polyvinyl acetate, polyvinyl alcohol, polyacrylic acid, polyacrylicamid, vinyl acetate-crotonic acid copolymer, vinylpyrrolidone-vinyl acetate copolymer, vinyl pyrrolidon-dimethylaminoethyl methacrylate copolymer, vinyl pyrrolidone-methacrylamidopropyl trimethyl ammonium chloride copolymer, methyl vinyl ether-maleic acid anhydride copolymer, acrylamid-β-methacrylyloxethyl trimethyl ammonium chloride copolymer, copolymers of acrylic acid dimethyldiallyl ammonium chloride, copolymer of acrylic acid methyl, ethyl, butyl or propylamide and acrylic acid methyl, ethyl, butyl or propyl ester, ethyl methacrylate oleylmethacrylate diethylaminoethyl methacrylate terpolymer, vinyl acetate vinylpropionate crotonic acid terpolymer, vinyl acetate crotonic acid polyethylenoxide terpolymer and vinyl pyrrolidon vinyl acetate-vinylpropionate terpolymer. Also, natural polymers, as for example chitosan or chitosan derivatives, Chinese balsamic resin and shellac can be used.

The polymerases and natural polymers used in the hair setting lotions are contained in appropriate quantities of 0.5 to 20 weight-%, particularly 1 to 10 weight-%, commonly used for these preparations.

These preparations contain the commonly used lower alcohols with 1 to 4 carbon atoms, for example ethyl alcohol and isopropyl alcohol, as an alcohol particularly for cosmetic purposes. These alcohols are contained in a quantity of 15 to 85 weight-%, preferably in a quantity of 25 to 75 weight-%. The hair setting lotions can have additional cosmetic hair additives, as for example perfume oils, herbal extracts, keratin hydrolysate, bactericidal or fungicidal substances, solubilizers for perfume oils, for example amphoteric or cationic surfactants, plastifying additives such as phthalic acid ester or alkylcitrate or hydrophobic substances, such as silicon oil, in a total quantity of up to 1 weight-%.

The hair setting lotions can also be available in form of an aerosol hair spray or aerosol hair lacquer; they then contain an additional 15 to 85 weight-% of a propellant and are filled into a pressurized container. Appropriate propellants are for example lower alkanes, as for example n-butane, i-butane, and propane or also their mixtures with dimethyl ether as well as propellants, which exist in a gaseous form at the pressures in question, such as N2, N2O and CO2, as well as mixtures of the propellants.

The hair setting lotion can also be available in form of a non-aerosol hair spray or non-aerosol hair lacquer, which can be sprayed with the aid of an appropriate mechanically operated spraying device. Mechanical spraying devices are understood to be those devices which allow the spraying of a liquid without the use of a propellant.

A spray pump or an elastic container provided with a spray valve, for example, can be used as suitable mechanical spraying device, into which the hair setting lotion is filled under pressure, wherein the elastic container expands and from which the lotion can be continually dispensed because of the contraction of the elastic container when the spray valve is opened.

The hair setting lotions preferably have a pH-value of 3 to 9.5. They are particularly preferred at an acid pH-value in the range of 3 to 6. In order to set this pH-value, citric acid, lactic acid or glycolic acid is preferably added.

In accordance with treatment step e) and if necessary after the application of the hair setting lotion, for stabilizing the hairstyle, the hair is preferably treated further in accordance with two alternative styling processes using higher temperatures in the range of 30° C.–55° C.

In accordance with the first styling process the hair is combed into the desired shape with a comb, a brush or with the fingers and at the same time or thereafter the tight curl of the hair ends is transformed into a big curl wave with the comb, a brush or with the fingers. In this case it is advantageous to use a big-toothed comb and to comb the hair carefully into the desired hairstyle. At the same time or thereafter the, as a rule still tight curl of the hair ends at that time, is carefully relaxed with a small-toothed comb, so that a natural big wave is created. A relaxation of a too tight curl may be particularly necessary at parts of the hair particularly damaged by chemicals or climactic influences (i.e. UV-rays), for example often at the forehead or the temples. Thus, in accordance with the process of the invention, the stylist can randomly correct the curl in both directions (larger or smaller) without haste and in this way achieves a visually controllable even wave already prior to neutralizing, a result which was previously impossible. Thus the safety and the reproduction of the wave result can be easily assured even with different hair textures.

Thereafter the hair shaped in this way is well dried at a higher temperature, particularly 30 to 45° C., preferably under a dryer hood with low air flow. After thorough drying, the naturalness of the wave allows a final visual control. Should the hair still show too strong a style-specific shape partially or at the ends (tight curl), the particular hair sections can be moistened or sprayed with water and can be once more slightly relaxed with the comb.

With the second styling process the hair is combed into the desired style with an appropriate device suitable for combing or styling at a higher temperature, particularly with a round brush that is heated electrically or by warmed-up air, or with a round brush and a blow dryer set at a higher temperature. A conventional hair dryer round brush can be used for this, wherein it is advantageous if it has a metal body, so that better heat conductivity is assured. The hair in this way is blow-dried in rollers or curlers as commonly practiced.

The temperature of the air flow of the blow dryer should be in the range of 30 to 55° C., wherein with normal hair a higher heat setting and with dyed hair a medium heat setting should be chosen.

The first and second styling process can also be combined, if desired. Principally a styling process at room temperature is also possible.

In a preferred embodiment of the process of the invention, the hair is first washed with a shampoo and then rinsed with water. Afterwards the balancing pre-wrap solution is applied evenly over the towel-dried hair. Then it is advantageous to allow the balancing pre-wrap solution to react at a higher temperature for 3 to 10 minutes, particularly for 5 minutes.

At the end of the reaction time the thus treated hair is rinsed out with water.

Then the hair is divided into single strands which are rolled onto rollers of a 5 to 10 millimeter diameter, preferably 5 to 12 millimeters.

Following the hair is treated with an adequate amount of a permanent shaping composition, preferably 60 to 150 grams, which, when compared to the commonly used permanent shaping compositions, is set at a slightly lower strength for the hair texture, in particular one which was described above.

After a sufficient reaction time necessary for the permanent shaping which, depending upon the nature of the hair, the pH-value and the shaping reaction of the shaping composition, as well the temperature used, takes 5 to 30 minutes (20 to 30 minutes without heat; 15 to 25 minutes with heat), the hair is rinsed with water.

Then the rollers are dabbed with a towel or an absorbent napkin, the hair is removed from the rollers and is styled in accordance with treatment step f) by using one of the two styling processes or a combination of the two. Preferably a hair setting lotion—as described above—is applied beforehand. The neutralizer for the subsequent treatment step g) is used, depending on hair thickness, in a preferred quantity of 80 to 100 grams.

For the oxidative treatment of treatment step g) any random neutralizer commonly used for such a treatment can be used. Examples for usable oxidizing agents in such neutralizers are potassium- and sodium bromate, sodium perborate, carbamide peroxide and hydrogen peroxide. The concentration of the oxidizing agent differs, depending on the usage time (as a rule 3 to 15 minutes) and the temperature in use. Normally the oxidizing agent in the ready-to-use aqueous post treatment preparation is available at a concentration of 0.4 to 10 weight-%, preferably 0.4 to 5 weight-% and has a pH-value of 2 to 7, preferably 2.2 to 3. The solution for the oxidative post treatment can contain additional substances of course, as for example wetting agents, care substances, such as cationic polymers, weak acids, buffer substances or peroxide stabilizers and can be available in form of an aqueous solution, an emulsion as well as in a thickened water-based form, particularly as cream, gel or paste. These common additives can be present in a post treatment preparation, particularly in a quantity of 0.1 to 10 weight-%.

The oxidative post treatment is particularly advantageous with a weakly concentrated neutralizer which for example merely contains 0.5 to 2 weight-% of hydrogen peroxide. In a particular development of the process 2 to 5 liters of a weakly concentrated neutralizer (i.e. an aqueous solution which contains 0.5 weight-% of hydrogen peroxide) are pumped from a basin with the aid of a pump in a repeated cycle onto the hair. A pump of this type is described for example in the published German patent application 36 43 417. Aside from this process a common neutralizer applicator, namely an applicator bottle with a spray head, can be used. During the application of the neutralizer, care should be generally used in order not to disturb the finished hairstyle. As a rule, this is possible with the application solution referred to, particularly when a hair setting lotion was applied to the hair beforehand. Such a hair setting lotion can then be omitted if necessary, if the neutralizer, if necessary, is sprayed on the hair in several steps. When using a gaseous oxidizing agent, particularly pure oxygen, the use of a hair setting lotion can also be omitted.

Contrary to all previous experiments, to imitate natural circumstances by modifying the known perm processes, the aforementioned process is distinguished by its gentleness and protection of the hair because of the use of chemically reactive substances in low concentration and while at the same time it still maintains the superior lasting changed shaped. An essential difference from the previous, commonly known perm processes, is that in addition neutralizing does not occur on the roller, but on the finished hairstyle.

The following examples are to explain the object of the invention in more detail, however, without limiting the subject to these examples.

EXAMPLES

Example 1

Normal, oxidatively untreated hair of 25 cm in length is washed and in a toweled-dry condition is sprayed with 12 ml of a balancing pre-wrap solution of the following mixture:

Balancing Pre-Wrap Solution

| | |
|---|---|
| 33.0 g | Buxus chinensis (jojoba oil) |
| 32.0 g | Helianthus annuus (sunflower oil) |
| 31.0 g | Persea gratissima (avocado oil) |
| 2.0 g | Hydrogenated castor oil ethoxylated with 40 ethylene oxide groups (Cremophor(R) RH40 of BASF) |
| 1.0 g | Hydrogenated castor oil ethoxylated with 7 ethylene oxide groups (Arlacel(R) 989 of ICI) |
| 0.1 g | Antioxidants |
| 0.9 g | Water |
| 100.0 g | |

The balancing pre-wrap solution is worked into the hair by hand, allowed to react for 5 minutes and then the hair is rinsed with a lot of water. Subsequently the hair is rolled on rollers with an 8 mm diameter (neck area) and 10 mm (rest of hair). Now 125 ml of a weakly alkaline (pH=8.0) permanent shaping composition of the following mixture is applied to the rollers.

Mildly Alkaline Permanent Shaping Composition

| | |
|---|---|
| 9.2 g | Ammonium thioglycolate |
| 2.5 g | Ammonium hydrogen carbonate |
| 1.0 g | Castor oil ethoxylated with 40 mol ethylene oxide |
| 1.0 g | Polydimethyl diallylammonium chloride |
| 1.0 g | Cocoamidopropyl betaine |
| 0.6 g | Perfume oil |
| 0.4 g | Ammonia, 25% aqueous solution |
| 84.3 g | Water |
| 100.0 g | |

The rolled hair is exposed for 20 minutes to an infrared radiation device in accordance with German Patent 40 18 186 (Climazon(R) of Ondal). The duration of the reaction time was determined through a test roller. Then the rolled hair is first rinsed with running water for 3 minutes and then the rollers are dabbed with a towel. The hair is unwound from the rollers and the rollers are removed. 10 ml of a hair setting lotion with a pH=3 of the following mixture are sprayed and distributed on the hair.

Hair Setting Lotion

| | |
|---|---|
| 0.30 g | Polyvinyl pyrrolidone |
| 0.20 g | 3-cocoamidopropyl 2-hydroxy 3-sulfopropyl dimethyl ammonium hydroxide (CTFA: cocoamidopropyl hydroxysultaine) |
| 0.20 g | Citric acid |
| 0.15 g | Cetyltrimethyl ammonium chloride |
| 0.10 g | Betaine |
| 0.10 g | Polyoxyethylene (45) polyoxypropylen (33) monobutyl ether (CTFA: PPG-33-Buteth-45) |
| 0.10 g | Glyceryl stearate |
| 0.10 g | Stearyl alcohol |
| 0.10 g | Keratin hydrolysate |
| 98.65 g | Water |
| 100.00 g | |

Now the individual hair strands are carefully combed into the desired hairstyle with a big-toothed comb. Particularly in the area of the forehead and the temples the too tight curl is carefully relaxed with a small-toothed comb, so that a natural, big curl wave is created. Thereafter the hair shaped in this way is heated and dried for 10 minutes (without a plastic cap) under a dryer hood at low air flow (medium blower setting) at 40° C. Since the curl was still too tight at the temples, the hair in this area was moistened a little (sprayed) and once more relaxed with a small-toothed comb. Subsequently 500 ml of a neutralizer of the following mixture are evenly applied over the hair from a conventional neutralizer applicator (applicator bottle with a spray head).

Neutralizer

| | |
|---|---|
| 1.00 g | Hydrogen peroxide |
| 0.02 g | Orthophosphoric acid |
| 0.01 g | Salicylic acid |
| 98.97 g | Water |
| 100.00 g | |

After allowing the neutralizer to react for 4 minutes, the hair is rinsed out with a lot of water for 2 minutes. Subsequently the hair is dried and is combed into the hairstyle or blow dried. The hair has received permanent, even, natural big curls.

Example 2

Medium-thick, oxidatively untreated hair of 20 cm in length is washed and in toweled-dry condition is sprayed with a balancing pre-wrap solution in accordance with Example 1. The balancing pre-wrap solution is worked into the hair by hand, allowed to react for 4 minutes, using an infrared radiation device and then the hair is rinsed with a lot of water. Subsequently the hair is rolled on rollers with an 7 mm diameter (neck area) and 9 mm (rest of hair). Now 81 ml of a "neutral" (pH=7.5) permanent shaping composition of the following mixture is applied to the rollers.

Neutral Permanent Shaping Composition from 2 Components

Component A

| | |
|---|---|
| 94.6 g | Ammonium thioglycolate, 70% aqueous solution |
| 5.4 g | Cysteine hydro chloride |
| 100.00 g | |
| | (pH = 6.0) |

Component B

| | |
|---|---|
| 0.8 g | Ammonia, 25% aqueous solution |
| 0.5 g | Ammonium hydrogen carbonate |
| 2.0 g | Lauryl alcohol, ethoxylated with 4 mol ethylene oxide |
| 1.0 g | Polydimethyl diallylammonium chloride |
| 1.0 g | Perfume oil |
| 0.5 g | Vinylpyrrolidon styrene mixed polymer |
| 0.5 g | Cetyltrimethyl ammonium chloride |
| 93.7 g | Water |
| 100.00 g | |

Component B has a pH-value of 8.5. Prior to use 15 g of Component A and 66 g of Component B are mixed with 81 g of the ready-to-use permanent shaping composition of pH=7.5.

The rolled hair is exposed for 22 minutes to an infrared radiation device in accordance with German Patent 40 18 186 (Climazon$^{(R)}$ of Ondal). Then the rolled hair is first rinsed with running water for 3 minutes and then the rollers are dabbed with a towel. The hair is unwound from the rollers and the rollers are removed. Now 9 ml of the hair setting lotion in accordance with Example 1 are sprayed and distributed over the hair.

Now the individual hair strands are carefully combed into the desired hairstyle with a big-toothed comb. Particularly in the area of the forehead and the temples the too tight curl is carefully relaxed with a small-toothed comb, so that a natural, big curl wave is created. Thereafter the hair shaped in this way is heated and dried for 10 minutes (without a plastic cap) under a dryer hood at low air flow (medium blower setting) at 40° C. Since the curl was still too tight at the temples, the hair in this area was moistened a little (sprayed) with water and once more relaxed with a small-toothed comb. Subsequently 500 ml of a neutralizer in accordance with Example 1 are evenly applied over the hair from a conventional neutralizer applicator (applicator bottle with a spray head).

After allowing the neutralizer to react for 5 minutes the hair is rinsed out with a lot of water for 2 minutes. Subsequently the hair is dried and combed into the hairstyle or blow dried. The hair has received permanent, even, natural big curls.

Example 3

Thick, oxidatively treated hair of 20 cm in length is washed and in toweled-dry condition is sprayed with 15 ml of a balancing pre-wrap solution in accordance with Example 1: The balancing pre-wrap solution is worked into the hair by hand, allowed to react for 4 minutes, using an infrared radiation device and the hair is rinsed with a lot of water. Subsequently the hair is rolled on rollers with an 8 mm diameter (neck area) and 10.5 mm (rest of hair). Now 125 ml of a weakly alkaline (pH=8.0) permanent shaping composition of the following mixture are applied to the rollers.

Weakly Alkaline Permanent Shaping Composition

| | |
|---|---|
| 7.0 g | Ammonium thioglycolate |
| 2.0 g | Ammonium hydrogen carbonate |
| 1.2 g | Lauryl alcohol ethoxylated with 40 mol ethylene oxide |
| 1.5 g | Polydimethyl diallyl ammonium chloride |
| 0.5 g | Cocoamidopropyl betaine |
| 0.8 g | Perfume oil |
| 0.2 g | Ammonia, 25% aqueous solution |
| 86.8 g | Water |
| 100.0 g | |

The rolled hair is exposed for 18 minutes to an infrared radiation device. Then the rolled hair is first rinsed with running water for 3 minutes and then the rollers are dabbed with a towel. The hair is unwound from the rollers and the rollers are removed. 12 ml of a hair setting lotion in accordance with Example 1 is sprayed and distributed over the hair.

Now the individual hair strands are carefully combed into the desired hairstyle with a blow dryer (medium heat setting=47 Degrees Celsius) and a round brush while being blow dried. Particularly in the area of the forehead and the temples the too tight curl is carefully relaxed with a round brush, so that a natural, big curl wave is created. Since the curl was still too tight at the temples, the hair in this area was moistened with a little water (sprayed) and once more relaxed with a small-toothed comb. Subsequently 500 ml of a neutralizer in accordance with Example 1 are evenly applied over the hair from a conventional neutralizer applicator (applicator bottle with a spray head).

After allowing the neutralizer to react for 4 minutes, the hair is rinsed out with a lot of water for 2 minutes. Subsequently the hair is dried and is combed into the hairstyle or blow dried. The hair has received permanent, even, natural big curls.

What is claimed is:

1. A process of permanent hair shaping, characterized in that
   a) the hair is rolled onto rollers,
   b) a permanent shaping composition based on a hair keratin reducing substance is applied to the rolled hair,
   c) the permanent shaping composition is left to act on the hair for 5 to 30 minutes,
   d) the permanent shaping composition is rinsed out with water,
   e) the rollers are unrolled and removed from the hair,
   f) the hair is styled,
   g) the styled hair is treated with a neutralizer based upon an oxidizing agent,
   h) the neutralizer is rinsed out of the hair after its reaction time.

2. The process in accordance with claim 1, characterized in that in treatment step f) the hair is combed into the desired shape with a comb, a brush, or with the fingers, and at the same time or thereafter the tight hair end curl is transformed into a big curl wave with a comb, a brush or with the fingers, and then the created hairstyle is dried at an increased temperature.

3. The process in accordance with claim 2, characterized in that the drying of the hairstyle in accordance with treatment step f) is performed at a higher temperature of 30 to 45 Degrees Celsius.

4. The process in accordance with claim 3, characterized in that a dryer hood is used for the creation of the higher temperature.

5. The process in accordance with claim 1, characterized in that the hair is washed with a shampoo prior to rolling it on rollers.

6. The process in accordance with claim 1, characterized in that the hair is treated with a balancing pre-wrap solution prior to rolling it on rollers.

7. The process in accordance with claim 6, characterized in that the balancing pre-wrap solution contains a reactive substance able to attach itself to damaged parts of the hair and reduces the reaction of the permanent shaping composition on the damaged parts of the hair.

8. The process in accordance with claim 7, characterized in that the reactive substance is a physiologically tolerated synthetic or natural hydrophobic oil or wax.

9. The process in accordance with claim 8, characterized in that the reactive substance is chosen from jojoba oil, avocado oil, sunflower oil, wheat germ oil, montan wax, mineral wax, vaseline and paraffin.

10. The process in accordance with claim 7, characterized in that the balancing pre-wrap solution consists of a mixture of physiologically tolerated synthetic or natural hydrophobic oil or wax and a solubilizer at a weight ratio of 50:1 to 2:1 or contains at least 5 weight-% of this mixture.

11. The process in accordance with claim 10, characterized in that the solubilizer is compound ethoxilated with 2 to 200 ethylene oxide group, selected from fatty acid, fatty acid ester, fatty acid amide, fatty acid amine or fatty alcohol with respectively 6 to 30 carbon atoms.

12. The process in accordance with claim 11, characterized in that the ethoxylated fatty acid ester is a castor oil ethoxilated with 5–60 ethylene oxide groups.

13. The process in accordance with claim 6, characterized in that the balancing pre-wrap solution is allowed to react at a higher temperature.

14. The process in accordance with claim 6, characterized in that the balancing pre-wrap solution is allowed to react for 3 to 10 minutes at a temperature of 30 to 45 Degrees Celsius.

15. The process in accordance with claim 1, characterized in that the rollers have a diameter of 5 to 20 mm.

16. The process in accordance with claim 1, characterized in that the hair keratin reducing substance is contained in the permanent shaping composition in an amount of 2 to 20 weight-%, and is chosen from thioglycolic acid, thiolactic acid, cysteine, cysteamine, alkyl- or acyl-cysteamine or sulfites.

17. The process in accordance with claim 1, characterized in that the hair keratin reducing substance is contained in the permanent shaping composition in an amount of 4 to 10 weight-%.

18. The process in accordance with claim 1, characterized in that the treatment step c) is performed at a temperature of from 30 to 45° degrees Celsius.

19. The process in accordance with claim 18, characterized in that an infrared radiation device or a dryer in combination with a foil cap is used to achieve the higher temperature.

20. The process in accordance with claim 19, characterized in that the reaction time of the permanent shaping composition is 20 to 25 minutes with normal, previously oxidatively untreated hair, and with oxidatively treated hair is 15 to 20 minutes.

21. The process in accordance with claim 1, characterized in that the exact reaction time of the permanent shaping composition is determined by means of a test roller.

22. The process in accordance with claim 1, characterized in that in treatment step f) the hair is combed into the desired hairstyle at increased temperature by means of an appropriate device for hairstyling at said increased temperature.

23. The process in accordance with claim 22, characterized in that combing into the desired hairstyle in treatment step f) is performed at a higher temperature of 30 to 55 Degrees Celsius.

24. The process in accordance with claim 22, characterized in that said appropriate device is a round brush heated electrically or by warm air.

25. The process in accordance with claim 22, characterized in that said appropriate device comprises a round brush and a blow dryer.

26. The process in accordance with claim 1, characterized in that the neutralizer is rinsed out with water or washed out with a shampoo.

27. The process in accordance with claim 1, characterized in that prior to treatment step f) a hair setting lotion based upon a hair setting polymer is applied to the hair.

28. The process in accordance with claim 27, characterized in that the hair setting lotion is a hairspray or a shaping lotion in form of an aqueous, water-based alcoholic or alcoholic preparation and contains 0.5 to 20 weight-% of the hair setting polymer.

29. The process in accordance with claim 27, characterized in that the hair setting polymer is chosen from the synthetic polymers polyvinyl pyrrolidone, polyvinyl acetate, polyvinyl alcohol, polyacrylic acid, polyacrylicamide, vinyl acetate crotonic acid copolymer, vinylpyrrolidone vinyl acetate copolymer, vinyl pyrrolidon dimethylaminoethyl methacrylate copolymer, vinyl pyrrolidone methacrylamidopropyl trimethyl ammonium chloride copolymer, methyl vinyl ether maleic acid anhydride copolymer, acrylamidmethacrylyloxethyl trimethyl ammonium chloride copolymer, acrylic acid dimethyldiallyl ammonium chloride copolymer, copolymer from acrylic acid methyl, ethyl, butyl or propylamide and acrylic acid methyl, ethyl, butyl or propyl ester, ethyl methacrylate oleylmethacrylate diethylaminoethyl methacrylate terpolymer, vinyl acetate vinylpropionate crotonic acid terpolymer, vinyl acetate crotonic acid polyethylenoxide terpolymer and vinyl pyrrolidon vinyl acetate-vinylpropionate terpolymer, and the natural polymers chitosan or chitosan, Chinese balsamic resin and shellac.

30. The process in accordance with claim 27, characterized in that the hair setting lotion has a pH-value in the range of 3 to 9.5.

31. The process in accordance with claim 1, characterized in that oxidizing agent contained in the neutralizer in treatment step g) is hydrogen peroxide is present at a concentration of 0.5 to 2 weight-%.

32. The process in accordance with claim 1, characterized in that the treatment in accordance with treatment step g) is performed with a gaseous oxidizing agent.

33. The process in accordance with claim 32, characterized in that the oxidizing agent is pure oxygen.

34. The process in accordance with claim 1, characterized in that oxidizing agent contained in the neutralizer in treatment step g) is present at a concentration of 0.4 to 10 weight-%, and is chosen from potassium- and sodium bromate, sodium perborate, carbamide peroxide and hydrogen peroxide.

35. The process in accordance with claim 1, characterized in that following the treatment step d) the rollers are daubed with an absorbent napkin or towel.

* * * * *